United States Patent
Hirsh et al.

(10) Patent No.: US 7,704,527 B2
(45) Date of Patent: Apr. 27, 2010

(54) MODIFIED RELEASE COMPOSITIONS OF MILNACIPRAN

(75) Inventors: Jane C. Hirsh, Wellesley, MA (US); Roman V. Rariy, Allston, MA (US); Shubha Chungi, Chestnut Hill, MA (US); Srinivas G. Rao, Encinitas, CA (US); Michael T. Heffernan, Hingham, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 0 days.

(21) Appl. No.: 12/211,780

(22) Filed: Sep. 16, 2008

(65) Prior Publication Data

US 2009/0018203 A1    Jan. 15, 2009

Related U.S. Application Data (63) Continuation-in-part of application No. 11/192,885, filed on Jul. 29, 2005, now abandoned, and a continuation-in-part of application No. 10/691,936, filed on Oct. 23, 2003, now abandoned, and a continuation-in-part of application No. 10/690,947, filed on Oct. 22, 2003, now abandoned.

(60) Provisional application No. 60/601,487, filed on Aug. 13, 2004, provisional application No. 60/592,254, filed on Jul. 29, 2004, provisional application No. 60/459,061, filed on Mar. 28, 2003, provisional application No. 60/443,237, filed on Jan. 28, 2003, provisional application No. 60/431,906, filed on Dec. 9, 2002, provisional application No. 60/431,626, filed on Dec. 5, 2002, provisional application No. 60/421,640, filed on Oct. 25, 2002.

(51) Int. Cl.
A61K 9/22 (2006.01)
A61K 9/20 (2006.01)
A61K 9/28 (2006.01)

(52) U.S. Cl. .................. 424/468; 424/464; 424/465; 424/474

(58) Field of Classification Search .................. None
See application file for complete search history.

(56) References Cited

U.S. PATENT DOCUMENTS 5,532,250 A    7/1996    Wong et al. .................. 514/415

(Continued)

FOREIGN PATENT DOCUMENTS

EP    0759299 A1    2/1997

(Continued)

OTHER PUBLICATIONS

"Milnacipran Significantly Improves Pain and Fatigue in Fibromyalgia Syndrome Patients", Retrieved from the Internet at: <http://fibromyalgiasupport.com/library/showarticle.cfm/id/4155> (Dec. 2002).

(Continued)

Primary Examiner—Humera N Sheikh
(74) Attorney, Agent, or Firm—Hunton & Williams LLP (57) ABSTRACT

A milnacipran formulation that provides delayed and extended release of milnacipran has been developed. The formulation comprises milnacipran or a salt thereof; an extended release excipient, and a delayed release excipient. The formulation provides, upon administration to a human subject, a $T_{max}$ of 4-10 hours.

17 Claims, 1 Drawing Sheet

U.S. PATENT DOCUMENTS

| | | | |
|---|---|---|---|
| 5,532,264 A | 7/1996 | Wong et al. | 514/432 |
| 5,532,268 A | 7/1996 | Wong et al. | 514/432 |
| 6,066,643 A | 5/2000 | Perry | |
| 6,380,200 B1 | 4/2002 | Mylari | |
| 6,441,038 B1 | 8/2002 | Loder et al. | 514/561 |
| 6,548,084 B2 | 4/2003 | Leonard et al. | |
| 6,602,911 B2 | 8/2003 | Kranzler et al. | 514/624 |
| 6,635,675 B2 | 10/2003 | Kranzler et al. | 514/620 |
| 6,667,060 B1 | 12/2003 | Vandecruys et al. | 424/488 |
| 6,699,506 B1 | 3/2004 | Paillard et al. | |
| 6,964,962 B2 | 11/2005 | Wong et al. | 514/239.2 |
| 6,992,110 B2 | 1/2006 | Kranzler et al. | 614/620 |
| 7,005,452 B2 | 2/2006 | Deregnaucourt et al. | 514/613 |
| 7,038,085 B2 | 5/2006 | Rariy et al. | 564/165 |
| 7,053,122 B2 | 5/2006 | Maw et al. | 514/649 |
| 7,074,833 B2 | 7/2006 | Deregnaucourt et al. | 514/617 |
| 7,175,854 B2 | 2/2007 | Dietrich et al. | 424/464 |
| 7,279,486 B2 | 10/2007 | Hashizume et al. | 514/278 |
| 7,309,799 B2 | 12/2007 | Buchwald et al. | 564/133 |
| 2002/0156067 A1 | 10/2002 | Wong et al. | 514/220 |
| 2002/0165246 A1 | 11/2002 | Holman | 514/270 |
| 2003/0203055 A1 | 10/2003 | Rao et al. | 424/738 |
| 2003/0232805 A1 | 12/2003 | Kranzler et al. | 514/217 |
| 2004/0019115 A1 | 1/2004 | Lassen et al. | 514/620 |
| 2004/0019116 A1 | 1/2004 | Kranzler et al. | 514/620 |
| 2004/0034101 A1 | 2/2004 | Rao et al. | 514/692 |
| 2004/0106681 A1 | 6/2004 | Rao et al. | 514/620 |
| 2004/0142904 A1 | 7/2004 | Rariy et al. | 514/63 |
| 2004/0229956 A1 | 11/2004 | Kranzler et al. | 514/619 |
| 2005/0009754 A1 | 1/2005 | Pan et al. | 514/19 |
| 2005/0032782 A1 | 2/2005 | Rao et al. | 514/220 |
| 2005/0059715 A1 | 3/2005 | Dooley et al. | 514/364 |
| 2005/0112199 A1 | 5/2005 | Padval et al. | |
| 2005/0119160 A1 | 6/2005 | Keith et al. | 514/2 |
| 2005/0153947 A1 | 7/2005 | Padval et al. | 514/171 |
| 2005/0153998 A1 | 7/2005 | Ito et al. | 514/278 |
| 2005/0192261 A1 | 9/2005 | Jost-Price et al. | 514/171 |
| 2005/0245519 A1 | 11/2005 | Barta et al. | 514/235.2 |
| 2005/0250775 A1 | 11/2005 | Fish et al. | 514/235.2 |
| 2005/0250803 A1 | 11/2005 | Glue et al. | 514/291 |
| 2005/0250818 A1 | 11/2005 | Koike et al. | 514/350 |
| 2005/0261369 A1 | 11/2005 | Mehlburger et al. | 514/540 |
| 2006/0003992 A1 | 1/2006 | Wong et al. | 514/220 |
| 2006/0014837 A1 | 1/2006 | Deregnaucourt et al. | 514/619 |
| 2006/0024365 A1 | 2/2006 | Vaya et al. | 424/468 |
| 2006/0030566 A1 | 2/2006 | Schelkun et al. | 514/249 |
| 2006/0128676 A1 | 6/2006 | Shafer et al. | 514/159 |
| 2006/0167032 A1 | 7/2006 | Galer et al. | 514/282 |
| 2006/0210633 A1 | 9/2006 | Dharmadhikari et al. | 424/473 |
| 2007/0010502 A1 | 1/2007 | Keith et al. | 514/171 |
| 2007/0066601 A1 | 3/2007 | Cremers et al. | 514/220 |
| 2007/0225375 A1 | 9/2007 | Kranzler et al. | 514/624 |
| 2008/0089859 A1 | 4/2008 | Holman | 514/171 |

FOREIGN PATENT DOCUMENTS

| | | |
|---|---|---|
| WO | WO 98/08495 | 3/1998 |
| WO | WO 99/59593 | 11/1999 |
| WO | WO 00/40224 | 7/2000 |
| WO | WO 03/101492 | 12/2003 |
| WO | WO 2004/039320 | 5/2004 |
| WO | WO 2004/105690 | 12/2004 |

OTHER PUBLICATIONS

Rao, "Pharmacological Therapies in Fibromyalgia", *Best Practice & Research Clinical Rheumatology*, vol. 17, Issue 4, pp. 611-627 (Aug. 2003).

O'Malley et al., "Treatment of Fibromyalgia with Antidepressants", *Journal of General Internal Medicine*, vol. 15, Issue 9, pp. 659-666, (Sep. 2000).

Nitu et al., "Emerging Trends in Pharmacotherapy of Chronic Pain", *Expert Opinion on Investigational Drugs*, vol. 12, No. 4, pp. 545-559 (Apr. 2003).

"Milnacipran Significantly Improves Pain in Patients with Fibromyalgia Syndrome Patients", *Inpharma*, vol. 1, No. 1412, pp. 7-7(1) (Oct. 28, 2003).

MODIFIED RELEASE COMPOSITIONS OF MILNACIPRAN

CROSS-REFERENCE TO RELATED APPLICATIONS

This application is a continuation-in-part of U.S. application Ser. No. 11/192,885, filed Jul. 29, 2005, which claims priority under 35 U.S.C. §119 to U.S. Appl. Ser. No. 60/601,487, filed Aug. 13, 2004 and U.S. Appl. Ser. No. 60/592,254, filed Jul. 29, 2004 and is a continuation-in-part of U.S. application Ser. No. 10/690,947, filed Oct. 22, 2003 and U.S. application Ser. No. 10/691,936, filed Oct. 23, 2003, both of which claim priority under 35 U.S.C. 119 to U.S. Appl. Ser. No. 60/458,995, filed Mar. 28, 2003; U.S. Appl. Ser. No. 60/458,994, filed Mar. 28, 2003; U.S. Appl. Ser. No. 60/459,061, filed Mar. 28, 2003; U.S. Appl. Ser. No. 60/443,618, filed Jan. 29, 2003; U.S. Appl. Ser. No. 60/443,237, filed Jan. 28, 2003; U.S. Appl. Ser. No. 60/431,861, filed Dec. 9, 2002; U.S. Appl. Ser. No. 60/431,906, filed Dec. 9, 2002; U.S. Appl. Ser. No. 60/431,627, filed Dec. 5, 2002; U.S. Appl. Ser. No. 60/431,626, filed Dec. 5, 2002; and U.S. Appl. Ser. No. 60/421,640, filed Oct. 25, 2002.

FIELD OF THE INVENTION

The present invention generally relates to milnacipran modified release compositions.

BACKGROUND OF THE INVENTION

Efficacy and tolerability are important factors determining the choice of a medication for treatment of mental depression and other mental disorders including Functional Somatic Disorders. The move from tricyclic antidepressants (TCAs) to selective serotonin reuptake inhibitors (SSRIs) involved not only the loss of the direct receptor interactions responsible for the adverse side effects of TCAs, but also the loss of the ability to inhibit the reuptake of norepinephrine. Selectivity for the single neurotransmitter serotonin may explain why SSRIs tend to be less efficacious than TCAs, especially in more severe forms of depression (Lopez-Ibor J. et al., 1996, Int. Clin. Psychopharm., 11:41-46). Older TCAs are associated with significant behavioral toxicity, notably psychomotor and cognitive impairment and sedation. SSRIs are largely devoid of these effects, but gastrointestinal disturbances such as nausea and dyspepsia are common with these agents (Hindmarch I., 1997, Human Psychopharmacology, 12:115-119). For example, for the widely prescribed SSRI sertraline (Zoloft®, Pfizer), the three most common adverse events associated with discontinuation of treatment were nausea, insomnia, and diarrhea (Physician's Desk Reference, 57th Edition, 2003, Thomson Medical).

Efforts toward improving antidepressant medications are guided by cumulative evidence from neurochemical and clinical studies supporting the therapeutic potential of enhancing monoamine function in depression. A number of antidepressant drugs have been developed based on their interaction with both serotonin (5-HT) and norepinephrine (NE) receptors. These serotonin and norepinephrine reuptake inhibitors (SNRIs) include duloxetine, venlafaxine, and milnacipran. Milnacipran is more appropriately referred to as a norepinephrine and serotonin reuptake inhibitor (NSRI) since its norepinephrine ("NE") to serotonin ("5-HT") ratio is 2:1 (Moret et al., 1985, Neuropharmacology, 24:1211-1219; Palmier et al., 1989, Eur. J. Clin. Pharmacol., 37:235-238). Current clinical evidence suggests that these new agents may offer improved efficacy and/or faster onset of action compared with SSRIs (Tran P. V. et al., 2003, J. Clin. Psychopharmacol., 23:78-86). Recent trials with the NSRI milnacipran suggest that this compound is effective in relieving pain both associated with, and independent of, depression (Briley M., 2003, Curr. Opin. Investig. Drugs, 4:42-45; Cypress Bioscience Inc., Cypress Bioscience Inc. Announces Final Results of Milnacipran Phase II Clinical Trial in Fibromyalgia, Media Release, Mar. 21, 2003, Available from: URL: (http://www.cypressbio.com).

Unfortunately these SNRI and NSRI compounds have demonstrated numerous side effects in human clinical trials. For example, the safety and tolerability of duloxetine (Cymbalta®, Eli Lilly and Company) was assessed in a pooled analysis of 7 double-blind trials involving 1032 patients treated with duloxetine (40-120 mg/day) and 732 patients treated with placebo. Adverse events which occurred at a rate of more than 5% for duloxetine were nausea, dry mouth, fatigue, dizziness, constipation, somnolence, decreased appetite, and sweating. Adverse events which led to discontinuation of treatment were nausea, dizziness, somnolence, dermatitis, insomnia, headache, and fatigue. Nausea and dizziness led to significantly more duloxetine-treated patients discontinuing treatment, compared with placebo (Mallinckrodt C. et al., American Psychiatric Association 2002 Annual Meeting, New Research Abstracts, 119, May 18, 2002; Detke M. J. et al., American Psychiatric Association 2002 Annual Meeting, New Research Abstracts, 33-34, May 18, 2002). Nausea was the only adverse event reported as a reason for discontinuation (Eli Lilly and Company, New Research Shows Cymbalta Reduces Anxiety Symptoms Associated with Depression, Media Release: Sep. 18, 2003).

For venlafaxine (Effexor®, Wyeth-Ayerst), a member of the SNRI family, the major reported side effects were those that affected the gastrointestinal system. In 4- to 8-week placebo-controlled clinical trials, treatment-emergent major gastrointestinal adverse experience incidence for Effexor® versus placebo (n=1,033 vs. 609) were: nausea (37% vs. 11%), constipation (15% vs. 7%), anorexia (11% vs. 2%), and vomiting (6% vs. 2%). In the same clinical trials, treatment-emergent major central nervous system adverse experience incidence were: somnolence (23% vs. 9%), dry mouth (22% vs. 11%), dizziness (19% vs. 7%), insomnia (18% vs. 10%), nervousness (13% vs. 6%), anxiety (6% vs. 3%), and tremor (5% vs. 1%). Importantly, nausea, in addition to being the most common reported side effect (see above), was the top reason venlafaxine patients in Phase 2 and Phase 3 depression studies discontinued treatment: almost 32% of patients who discontinued treatment did so due to nausea (Physician's Desk Reference, 57th Edition, 2003, Thomson Medical).

Milnacipran (Ixel®, Pierre Fabre), has demonstrated numerous adverse reactions in human clinical trials with tolerability decreasing with increasing dose (Puech A. et al., 1997, Int. Clin. Psychopharm., 12:99-108). In the double-blind, randomized, multicenter clinical study the most frequent spontaneously reported adverse events for 100 mg/day milnacipran twice daily were as follows: abdominal pain (13%), constipation (10%), and headache (9%). Interestingly, when in the same study milnacipran was given 200 mg/day twice daily, pain related adverse reactions decreased (headache to 8% and abdominal pain to 7%) but nausea and vomiting were more pronounced side effects and were reported by 7% of the patients (Guelfi J. D., 1998, Int. Clin. Psychopharm., 13:121-128). In a double-blind comparative study involving 219 elderly patients with depression the only adverse event reported more frequently for milnacipran recipients than for TCA imipramine recipients was nausea.

Patients received either milnacipran or imipramine 75-100 mg/day twice daily for 8 weeks (Tignol J. et al., 1998, Acta Psychiatrica Scandinavica, 97:157-165). It was also observed that when milnacipran was administered intravenously to 10 patients, five of them reported transient nausea. Nausea was primarily reported at the moment of peak of milnacipran plasma level (Caron J. et al., 1993, Eur. Neuropsychopharmacol., 3:493-500). This study clearly demonstrates that nausea is directly correlated with milnacipran blood plasma concentration. In addition, it strongly suggests that the nausea can be a centrally mediated side effect since the drug was given intravenously in this study. Data from other studies suggest that milnacipran may also induce a locally mediated nausea via gastric irritation (the rapid onset of the nausea was observed even prior to achieving peak plasma levels).

The incidence of spontaneously reported milnacipran adverse experiences in placebo-controlled clinical trials is given in Table 1 (adverse effect is listed if frequency was more than 2% in milnacipran 100 mg/day group). It is clearly seen from the data presented in Table 1, that the incidence of certain adverse events, including nausea, vomiting, sweating, hot flashes, palpitations, tremors, anxiety, dysuria, and insomnia, increase with dosage.

TABLE 1

Incidence of spontaneously reported milnacipran adverse experiences in placebo-controlled clinical trials

| Adverse Event | Placebo N = 394 | Frequency of Adverse Experiences (%) | | |
|---|---|---|---|---|
| | | 50 mg/day twice daily N = 426 | 100 mg/day twice daily N = 1871 | 200 mg/day twice daily N = 865 |
| Nausea | 10.9 | 12.7 | 11.2 | 19.4* |
| Headache | 17.0 | 14.6 | 8.4 | 13.5 |
| Increased Sweating | 1.3 | 14.0 | 4.3* | 11.6* |
| Constipation | 4.3 | 8.0 | 6.5 | 11.4* |
| Insomnia | 10.7 | 9.2 | 6.1 | 11.3 |
| Dry mouth | 5.6 | 9.4 | 7.9 | 9.0 |
| Vomiting | 3.6 | 3.8 | 3.9 | 7.9* |
| Abdominal Pain | 5.1 | 6.1 | 6.5 | 7.6 |
| Tremor | 1.5 | 0.9 | 2.5 | 6.7* |
| Anxiety | 1.3 | 2.8 | 4.1 | 5.1 |
| Palpitations | 1.8 | 2.3 | 2.7 | 4.6 |
| Vertigo | 1.8 | 1.6 | 5.0 | 4.5 |
| Fatigue | 3.0 | 2.8 | 2.5 | 4.4 |
| Dysuria | 0.3 | 1.4 | 2.1* | 3.7* |
| Hot flushes | 0 | 1.6 | 3.0 | 3.6 |
| Somnolence | 3.8 | 5.4 | 2.3 | 3.5 |
| Agitation | 3.0 | 1.6 | 3.3 | 2.9 |
| Nervousness | 2.0 | 4.2 | 2.0 | 2.8 |
| Dyspepsia | 4.1 | 3.5 | 2.1 | 2.2* |

*Significantly greater than placebo

It is important to note that in one of the early depression trials, even after one week of milnacipran dose escalation employed to reduce side effects, the most commonly reported reason for discontinuation of treatment because of adverse effects was nausea and vomiting (Leinonen E., 1997, Acta Psychiatr. Scand., 96:497-504). In the recent fibromyalgia clinical trial with the long dose escalation period (four weeks), which was implemented in order to reduce milnacipran side effects and increase patient's tolerance, the most common dose-related side effect reported by patients was nausea (Cypress Bioscience Inc., Cypress Bioscience Inc. Announces Final Results of Milnacipran Phase II Clinical Trial in Fibromyalgia, Media Release, Mar. 21, 2003).

The data presented in Table I demonstrates that the currently available immediate release formulation of milnacipran is not ideal for the treatment of medical conditions that require milnacipran doses equal or above 100 mg/day given either once a day or twice a day due to high incidence of treatment-emergent side effects that leads to poor patient tolerance. Higher doses are required in the treatment of severe depression and other associated disorders. As shown in one of the early antidepressant clinical trials, milnacipran dosages of 200 mg/day were superior to lower doses (Von Frenckell R et al., 1990, Int. Clin. Psychopharmacology 5:49-56). Milnacipran dosing regimes of 100-250 mg daily were recently reported for the treatment of fibromyalgia (U.S. Pat. No. 6,602,911). It would be very difficult to reach the upper limits of the dose range using the currently available formulation due to the dose related treatment emergent side effects and the need to titrate over a long period of time to reach the required dose.

Moreover, an immediate release formulation of milnacipran may not be suitable for a once-daily dosing regimen for treatment of depression due to milnacipran's relatively short half-life, which is approximately 8 hours, (Ansseau M. et al., 1994, Psychopharmacology 114:131-137). Milnacipran's relatively short half-life could also be responsible for the observation that twice-a-day administration (versus once-a-day) of immediate release formulation in fibromyalgia trials resulted in pain improvement statistically superior to that of placebo treatment (Cypress Bioscience Inc., Cypress Bioscience Inc. Announces Final Results of Milnacipran Phase II Clinical Trial in Fibromyalgia, Media Release, Mar. 21, 2003).

Merely stating that a drug can be administered using a sustained release formulation is not sufficient. For example, U.S. Pat. No. 6,602,911 to Kranzler et al. states "for administration orally, the compounds may be formulated as a sustained release preparation". While the above patent references formulation techniques, only WO98/08495 by Paillard B. et al. provides specific sustained release formulations of milnacipran. However, Paillard does not describe diminishing locally and/or centrally mediated side effects. Only by careful understanding of the relationship of the therapeutic dose to plasma levels can a modified dosage form be designed that will reduce, diminish, or prevent locally mediated as well a centrally mediated side effects. Paillard describes a prolonged release formulation of milnacipran with dosages ranging from 60-240 mg, in which 10-55% of the total dose is released within two hours. The prolonged release formulation consists of saccharose and/or starch minigranules coated with the active drug and then coated with at least one water-insoluble polymer that is permeable to physiological fluids.

U.S. Pat. No. 6,066,643 to Perry describes a method of potentiating the therapeutic action of an SSRI, for example milnacipran, by coadministering the SSRI with monoxidine. Perry suggests alleviating or diminishing side effects of a SSRI by co-formulating an SSRI in a "quick, sustained, or delayed release" formulation with a centrally acting antihypertensive agent. The administration of the latter compound to humans is associated with drowsiness, headache and dry mouth. Perry's approach may result in additional side effects experienced by patients.

It is therefore an object of the present invention to provide milnacipran formulations which will lower the incidence and intensity of side effects, especially for higher dosages, and lower or reduce the frequency of dosing and the need to slowly titrate the drug in order to achieve the therapeutic dose levels required for treatment of these disorders.

It is therefore an object of the present invention to provide milnacipran formulations that produce a therapeutic effect over approximately 24 hours when administered to a patient in need, wherein the release rate and dosage are effective to provide relief from at least one disorder selected from the group consisting of depression, fibromyalgia syndrome, chronic fatigue syndrome, pain, attention deficit/hyperactivity disorder, and visceral pain syndromes (VPS) such as irritable bowel syndrome (IBS), noncardiac chest pain (NCCP), functional dyspepsia, interstitial cystitis, essential vulvodynia, urethral syndrome, orchialgia, affective disorders including depressive disorders (major depressive disorder, dysthymia, atypical depression) and anxiety disorders (generalized anxiety disorder, phobias, obsessive compulsive disorder, panic disorder, post-traumatic stress disorder), premenstrual dysphoric disorder, temperomandibular disorder, atypical face pain, migraine headache, and tension headache, with diminished incidence or reduced intensity of common milnacipran side effects reported for immediate release formulation.

It is a further object of the present invention to provide formulations that provide alternative pharmacokinetic release profiles that eliminate or diminish unwanted side effects and the current need to slowly increase (titrate) doses in order to achieve the desired therapeutic dose.

It is still another object of the present invention to provide a formulation that provides a unit dose between 25 and 500 mg which provides for flexibility in morning or evening administration.

SUMMARY OF THE INVENTION

A once-a-day oral milnacipran modified release composition has been developed. The milnacipran composition, when administered orally, first passes through the stomach releasing less than 10% of the total milnacipran dose. The composition then enters the intestines where the drug is released slowly over an extended period of time. The release profile is characterized by a 0.05 to four hour lag time period during which less than 10% of the total milnacipran dose is released into the stomach followed by a slow or extended release of the remaining drug within the intestines over a defined period of time. The composition provides in vivo drug plasma levels characterized by $T_{max}$ at 4-10 hours and, optionally, an approximately linear drop-off thereafter, and $C_{max}$ below 3000 ng/ml, preferably below 2000 ng/ml, and most preferably below 1000 ng/ml. The composition produces a therapeutic effect over approximately 24 hours when administered to a patient in need, resulting in diminished incidence or decreased intensity of common milnacipran side effects such as nausea, vomiting, sleep disturbance, headache, tremulousness, anxiety, panic attacks, palpitations, urinary retention, orthostatic hypotension, diaphoresis, chest pain, rash, weight gain, back pain, constipation, vertigo, increased sweating, agitation, hot flushes, tremors, fatigue, somnolence, dyspepsia, dysoria, nervousness, dry mouth, abdominal pain, irritability, and insomnia.

DETAILED DESCRIPTION OF THE INVENTION

Definitions

Delayed release dosage form: A delayed release dosage form is one that releases a drug (or drugs) at a time other than promptly after administration.

Extended release dosage form: An extended release dosage form is one that allows at least a twofold reduction in dosing frequency as compared to the drug presented as a conventional dosage form (e.g. as a solution or prompt drug-releasing, conventional solid dosage form).

Modified release dosage form: A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Matrix-forming materials: Matrix forming materials are materials which form strong, viscous gels upon hydration and provide control of drug diffusion and release. In hydrophilic matrix systems, matrix forming materials are uniformly incorporated throughout the tablet. Upon contact with water, the outer tablet layer is partially hydrated, forming a gel layer. The rate of diffusion of the drug(s) out of the gel layer and the rate of erosion of the gel layer determine overall tablet dissolution and drug delivery rates. Examples of matrix forming materials include cellulose ethers that are water-soluble such as methylcellulose, ethyl cellulose and hydroxypropyl methylcellulose.

Modified Release Milnacipran Formulations

The milnacipran composition incorporates two types of modified-release dosage forms, namely delayed release and extended release.

The delayed-release portion is designed to prevent drug release in the upper part of the gastrointestinal (GI) tract. Delayed release can be achieved using enteric coatings. The enteric coated formulation remains intact or substantially intact in the stomach but dissolves and releases the contents of the dosage form once it reaches the small intestine. The purpose of an enteric coating is to delay the release of milnacipran within the stomach, thereby avoiding nausea, vomiting, or bleeding due to irritation of the gastric mucosa, which could otherwise occur.

The delay in the release of milnacipran postpones the rise of milnacipran in the blood plasma for up to 4 hours after oral administration, hence allowing for bed time (PM) administration. The milnacipran blood plasma level for once-a-day formulation is at a minimum 24 hours after the dose is taken. Since the intensity of centrally mediated side effects is a function of drug blood plasma level, it is expected that the intensity of side effects would be the lowest 24 hours after the last dose is taken. Milnacipran patients taking immediate release formulations twice-a-day and suffering from insomnia would be able to significantly decrease this side effect associated with milnacipran treatment by switching to PM administration. A once-a-day formulation when taken at bed time provides up to about a four-hour window during which essentially no drug is released, allowing a patient to fall a sleep and most likely enter the rapid eye movement (REM) sleep. Since milnacipran induces only minor disturbances of REM sleep compared with SSRIs and tricyclic antidepressants (Gervasoni D. et al., 2002, Pharmacol. Biochem. Behav., 73:557-563), minimal sleep disturbances are expected when the formulation is administered at bed time.

Thus a once-a-day modified release milnacipran formulation provides the versatility of AM or PM dosing.

The milnacipran extended-release portion extends and maintains drug release within the intestines over a period of time before returning to the steady-state level at night time to avoid sleep disturbances. As used herein, "about" means approximately plus or minus ten percent.

The expected therapeutic benefit of these formulations is further supported by the results of a 12-week randomized, double-blind placebo-controlled dose escalation monotherapy trial that evaluated milnacipran in patients with a diagnosis of Fibromyalgia Syndrome (FMS) presented by Cypress Bioscience, Inc. at the 41$^{st}$ Annual Meeting of American College of Neuropsychopharmacology, San Juan, Puerto Rico (Gendreau R. M. et al., Dec. 9, 2002, Poster presentation, Poster# 85 "Development of milnacipran, a dual reuptake inhibitor for treatment of chronic pain associated with fibromyalgia").

In the FMS trial conducted by Cypress Bioscience, all patients were escalated over a 4-week period in weekly steps from 25 mg daily, to 50, 100, and finally 200 mg daily, or until dose-limiting toxicity was evident. The current available immediate release (IR) milnacipran formulation was used as the only milnacipran dosage form in this study. Patients who successfully reached the 200 mg daily dose were then treated for an additional 8 weeks at that dose. It is important to emphasize that at any given dose level, milnacipran once daily (QD-IR) patients received the full dose of immediate release milnacipran in the morning and received a placebo at night. Milnacipran twice daily (BID-IR) patients received the same total amount in a split dose, given morning and evening.

The primary endpoint used by Cypress Bioscience was defined as the change in pain score from baseline to endpoint based on pain scores collected on the patient electronic diary. Endpoint was defined as week twelve for assessments with a single value (such as clinical measures) or the average of scores at weeks 11 and 12 for diary-based outcomes. It was shown that milnacipran effectively treated pain associated with fibromyalgia syndrome and, additionally, improved mood in depressed patients with FMS. The improvement in pain scores reported by study participants, when the 200 mg daily dose was reached, indicates that this substantially higher dose is needed for the alleviation of pain. On a scale of 1-7, where 1 was very much improved, 4 was unchanged, and 7 was very much worse, the mean global pain score for all milnacipran patients who reached endpoint at the time of the analysis was 2.3. In contrast, the mean value for placebo patients was 4.3 (the difference between the milnacipran groups and placebo is statistically significant at p=0.0001). It is important to note that, within the milnacipran groups, twice daily dosing was significantly more effective than once daily dosing in pain reduction. Twice daily dosing regimens, in addition to being more therapeutically effective, also demonstrated fewer dose-related adverse events and resulted in a lower rate of dose intolerance than once daily regimen (19% of participants in QD-IR group failed the dose escalation vs. only 6% in BID-IR group). Note that no dose escalation failures were recorded in the placebo group.

These clinical differences between QD-IR and BID-IR are most likely due to the distinct differences in the drug plasma levels (especially $C_{max}$) that these two dosing regiments support. The BID-IR dosing regimen supports drug plasma levels characterized by lower $C_{max}$ and lower drug plasma fluctuations over a 24 hour period than that of QD-IR. When a daily dose is administered QD-IR, the $C_{max}$ is approximately two times higher than that of BID-IR dosing regimen. Higher $C_{max}$ causes an increase in the severity of the adverse side effects (which may also interfere with the objective pain level self-assessment by the patient) and leads to lower drug tolerance and less patient compliance. Therefore, the observed superior milnacipran performance when the drug was administered BID-IR is thought to be due to more "sustained" drug plasma levels over a 24 hour period.

Based on the clinical trial data obtained and presented by Cypress Bioscience, sleep quality improves, albeit marginally, when milnacipran was administered BID-IR. This could be interpreted as another indication that the formulation that provides more "sustained" drug plasma levels over a 24 hour period should demonstrate superior performance when compared to standard immediate release formulation and, importantly, cause less insomnia.

Milnacipran

Milnacipran and methods for its synthesis are described in U.S. Pat. No. 4,478,836 to Mouzin et al. Milnacipran (midalcipran, midacipran, F 2207) inhibits the uptake of both norepinephrine (NE) and serotonin (5-HT), with an NE to 5-HT ratio of 2:1 (Moret et al., 1985, Neuropharmacology, 24:1211-1219; Palmier et al., 1989, Eur. J. Clin. Pharmacol., 37:235-238) but does not affect the uptake of dopamine. Milnacipran has no affinity for alpha or beta adrenergic, muscarinic, histaminergic, and dopaminergic receptors. This suggests that milnacipran has a low potential to produce anticholinergic, sedative, and stimulant effects. Milnacipran does not affect the number of beta adrenoceptors in rat cortex after chronic administration (Briley M. et al., Int. Clin. Psychopharmac., 1996, 11:10-14). Additional information regarding milnacipran may be found in the Merck Index, 12$^{th}$ Edition, at entry 6281.

As used herein "milnacipran" also encompasses pharmaceutically acceptable, pharmacologically active derivatives of milnacipran including both individual enantiomers of milnacipran (dextrogyral and levrogyral enantiomers) and their pharmaceutically acceptable salts, mixtures of milnacipran enantiomers and their pharmaceutically acceptable salts, and active metabolites of milnacipran (e.g., para-hydroxy-milnacipran (F2782), individual enantiomers of para-hydroxy-milnacipran, mixtures of enantiomers of para-hydroxy-milnacipran, or pharmaceutically acceptable salts thereof) and their pharmaceutically acceptable salts, unless otherwise noted. It is understood that in some cases dosages of enantiomers, derivatives, and metabolites may need to be adjusted based on relative activity of the racemic mixture of milnacipran.

As used herein, "pharmaceutically acceptable salts" refer to derivatives of the disclosed compounds wherein the parent compound is modified by making the acid-addition or base-addition salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the term "stereoisomers" refers to compounds made up of the same atoms bonded by the same bonds but having different spatial structures which are not interchangeable. The three-dimensional structures are called configurations. As used herein, the term "enantiomers" refers to two stereoisomers whose molecules are nonsuperimposable mirror images of one another. As used herein, the term "optical isomer" is equivalent to the term "enantiomer". The terms "racemate", "racemic mixture" or "racemic modification" refer to a mixture of equal parts of enantiomers. The term "chiral center" refers to a carbon atom to which four different groups are attached. The term "enantiomeric enrichment" as used herein refers to the increase in the amount of one enantiomer as compared to the other. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization of diastereomeric salts/derivatives or preparative chiral chromatography.

Combinations with Other Active Compounds

Milnacipran can be administered adjunctively with other active compounds such as analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

Specific examples of compounds that can be adjunctively administered with milnacipran include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenyloin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

By adjunctive administration is meant simultaneous administration of the compounds, in the same dosage form, simultaneous administration in separate dosage forms, and separate administration of the compounds.

Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, matrix-forming compositions and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—

The science and practice of pharmacy", 20th ed., Lippincott Williams & Wilkins, Baltimore, Md., 2000, and "Pharmaceutical dosage forms and drug delivery systems", 6$^{th}$ Edition, Ansel et. al., (Media, Pa.: Williams and Wilkins, 1995) which provides information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristo-amphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

The amount of active agent released in each dose will be a therapeutically effective amount. In the case of milnacipran, the total amount in the dosage form is in the range of approximately 25 to 500 mg.

Extended Release Dosage Forms

The extended release formulations are generally prepared as described in "Remington—The science and practice of pharmacy" (20th ed., Lippincott Williams & Wilkins, Baltimore, Md., 2000) using extended release excipients. Exemplary extended release excipients include, but are not limited to, insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and cross-linked acrylic acid polymers like Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit®RS30D, respectively. Eudragit®RL30D and Eudragit®RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit®RL and 50% Eudragit® RS, and 10% Eudragit®g RL and 90% Eudragit®g RS. One skilled in the art will recognize that other acrylic polymers may also be used, such as, for example, Eudragit® L.

In some embodiments, the extended release formulations can be prepared using osmotic systems or by applying a semi-permeable coating to the dosage form. In the latter case, the desired drug release profile can be achieved by combining low permeable and high permeable coating materials in suitable proportion. In other embodiments, the extended release formulations can be prepared using a diffusion system. Diffusion systems typically consist of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds.

The devices with different drug release mechanisms described above can be combined in a final dosage form comprising single or multiple units. Examples of multiple units include, but are not limited to, multilayer tablets and capsules containing tablets, beads, or granules.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations are created using delayed release excipients, for example by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragit® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Kit Containing Delayed Release/Extended Release Formulations

A kit is provided wherein the once a day modified release dosage form is packaged to provide a method to conveniently begin dose titration at lower doses, for example, beginning at 25 mg, gradually increasing to 50 mg, 75 mg, 100 mg, 200 mg, 400 mg, 500 mg, over a period ranging from three days up to 16 weeks. The packaging material may be a box, bottle, blister package, tray, or card. The kit will comprise different dosage units of milnacipran to allow for dosage escalation. Thus, for example, the kit will include a package insert instructing the patient to take a specific dose at a specific time, for example, a first dose on day one, a second higher dose on day two, a third higher dose on day three, and so on, until a maintenance dose is reached.

Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily, incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6$^{th}$ Ed. (Media, Pa.: Williams & Wilkins, 1995).

Alternatively, a delayed release tablet may be formulated by dispersing the drug within a matrix of a suitable material such as a hydrophilic polymer or a fatty compound. The hydrophilic polymers may be comprised of polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

A preferred method for preparing extended release tablets is compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming an extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

All publications cited are incorporated by reference.

Administration of Milnacipran Formulations

The formulation can be administered to any patient in need thereof. Although preferred patients are human, typically any mammal including domestic animals such as dogs, cats and horses, may also be treated.

The amount of the active ingredients to be administered is chosen based on the amount which provides the desired dose to the patient in need of such treatment to alleviate symptoms or treat a condition.

Milnacipran has been used as an antidepressant in approximately 400,000 patients, and is known to be non-toxic in humans. Pharmacokinetic studies have shown that oral doses of milnacipran are rapidly absorbed and extensively distributed in the body within 1-2 hours. Maximum plasma levels are quickly reached, with a half-life in humans of approximately 8 hours. Metabolism in the liver leads to the formation of ten chemically identified metabolites, although these metabolites represent only about 10% of the concentration of the parent drug. In humans, 90% of the parent drug is eliminated unchanged via the kidneys. This pharmacokinetic profile gives milnacipran certain pharmacokinetic advantages, such as low inter-individual variation in plasma levels, low potential for drug interactions, and limited impact on hepatic cytochrome P-450 systems. These pharmacokinetic properties differentiate milnacipran from most other antidepressant drugs and contribute to the strong safety profile of milnacipran (Puozzo C. et al., 1996, Int. Clin. Psychopharmacol., 11:15-27; Caccia S., 1998, Clin. Pharmacokinet., 34:281-302; Puozzo C. et al., 1998, Eur. J. Drug Metab. Pharmacokinet., 23:280-286).

Milnacipran can be administered for the treatment of depression, fibromyalgia syndrome, chronic fatigue syndrome, pain, attention deficit/hyperactivity disorder, and visceral pain syndromes (VPS) such as irritable bowel syndrome (IBS), noncardiac chest pain (NCCP), functional dyspepsia, interstitial cystitis, essential vulvodynia, urethral syndrome, orchialgia, affective disorders including depressive disorders (major depressive disorder, dysthymia, atypical depression) and anxiety disorders (generalized anxiety disorder, phobias, obsessive compulsive disorder, panic disorder, post-traumatic stress disorder), premenstrual dysphoric disorder, temperomandibular disorder, atypical face pain, migraine headache, and tension headache.

Adverse reactions to the oral administration of milnacipran typically include at least one of the following: nausea, vomiting, headache, dyspepsia, abdominal pain, insomnia, tremulousness, anxiety, panic attack, palpitations, urinary retention, orthostatic hypotension, diaphoresis, chest pain, rash, weight gain, back pain, constipation, vertigo, increased sweating, agitation, hot flushes, tremors, fatigue, somnolence, dysoria, nervousness, dry mouth, and irritability.

The vomiting reflex is triggered by stimulation of chemoreceptors in the upper GI tract and mechanoreceptors in the wall of the GI tract which are activated by both contraction and distension of the gut wall as well as by physical damage. A coordinating center in the central nervous system controls the emetic response. The center is located in the parvicellular reticular formation in the lateral medullary region of the brain. Afferent nerves to the vomiting center arise from the abdominal splanchic and vagal nerves, vestibule-labyrinthine receptors, the cerebral cortex and the chemoreceptors trigger zone (CTZ). The CTZ lies adjacent in the area postrema and contains chemo-receptors that sample both blood and cerebrospinal fluid. Direct links exist between the emetic center and the CTZ. The CTZ is exposed to emetic stimuli of endogenous origin and to stimuli of exogenous origin such as drugs. The efferent branches of the cranial nerves V, VII, and IX, as well as the vagus nerve and sympathetic trunk produce the complex coordinated set of muscular contractions, cardiovascular responses and reverse peristalsis that characterizes vomiting. The area postrema is rich in dopamine receptors as well as 5-hydroxytryptamine (5HT) receptors.

When administered orally, the extended release formulation first passes through the stomach, releasing 0-10% of the total milnacipran dose and then enters the intestines where the drug is released slowly. The release profile is typically characterized by a 0.05-4 hour lag time period during which about 0-10% of the total milnacipran dose is released followed by a slow or extended drug release. The pharmaceutical composition of milnacipran provides the in vivo drug plasma levels characterized by $T_{max}$ at 4-10 hours, preferably at 5-8 hours and an approximately linear drop-off sometime thereafter and $C_{max}$ below 3000 ng/ml, preferably below 2000 ng/ml, and most preferably below 1000 ng/ml. This dosage form offers many advantages when compared to immediate release delivery systems, such as minimization of peak-trough-fluctuations, avoidance of undesirable side effects and/or lowering their intensity/severity, reduced frequency of administration and improved patient compliance.

This formulation is designed to be administered once-a-day to a patient in need thereof, so that a therapeutic effect is provided over approximately 24 hours, with diminished incidence or decreased intensity of one or more common milnacipran side effects such as nausea, vomiting, headache, tremulousness, anxiety, panic attacks, palpitations, urinary retention, orthostatic hypotension, diaphoresis, chest pain, rash, weight gain, back pain, constipation, vertigo, increased sweating, agitation, hot flushes, tremors, fatigue, somnolence, dyspepsia, dysoria, nervousness, dry mouth, abdominal pain, irritability, and insomnia.

EXAMPLES

The present invention will be further understood by reference to the following non-limiting examples.

Example 1

Preparation of a Delayed Release/Extended Release Milnacipran Tablet Using Aqueous Granulation The ingredients, manufacturing process, and in vitro dissolution data for the extended release portion of a delayed release/extended release milnacipran pharmaceutical composition are described below (Lot# 1, small scale manual batch):

| INGREDIENTS | mg per tablet |
| --- | --- |
| Milnacipran HCl | 120 |
| Hydroxypropyl Methylcellulose E10M | 150 |
| Ethyl cellulose 10 cps | 70 |
| Dibasic Calcium phosphate, Dihydrate | 100 |
| Povidone K 90 | 8 |
| Magnesium stearate | 6 |
| Total tablet weight | 454 |

A wet granulation process consisting of the steps of dry blending, wet granulation, drying, size reduction, and final blending with a lubricant was utilized on a bench scale. The tablets were compressed using a single station bench top model tablet press.

Dissolution in Phosphate Buffer pH 6.8

| | Dissolution time, hours | | | | | | | | |
| --- | --- | --- | --- | --- | --- | --- | --- | --- | --- |
| | 0.5 | 1 | 2 | 4 | 6 | 8 | 10 | 12 | 14 | 16 |
| Milnacipran released, % of total dose | 19 | 27 | 38 | 53 | 63 | 71 | 76 | 80 | 82 | 85 |

A USP dissolution apparatus I (rotating baskets at 100 rpm), filled with pH 6.8 phosphate buffer, was used for the dissolution experiments. Experiments were carried out at 37° C. The analysis of the dissolution samples was performed using the ultraviolet ("UV") method.

Example 2

Preparation of an Alternative Delayed Release/Extended Release Milnacipran Tablet Using Alcohol Granulation The ingredients, manufacturing process, and in vitro dissolution data for the extended release portion of an alternative delayed release/extended release milnacipran pharmaceutical composition are described below (Lot# 2, small scale manual batch).

| INGREDIENTS | mg per tablet |
| --- | --- |
| Milnacipran HCl | 200 |
| Lactose | 150 |
| Hydroxypropyl methylcellulose K15M | 150 |
| Povidone K 90 | 10 |
| Magnesium stearate | 5 |
| Total tablet weight | 515 |

The wet granulation process was performed as described in Example 1, only alcohol was used for wet granulation step. The tablets were compressed using a single station bench top model tablet press.

Dissolution in Deionized ("DI") Water

| | Dissolution time, hours | | | | | | | |
| --- | --- | --- | --- | --- | --- | --- | --- | --- |
| | 0.5 | 1 | 2 | 4 | 6 | 8 | 10 | 12 | 14 |
| Milnacipran released, % of total dose | 14 | 22 | 33 | 48 | 59 | 67 | 72 | 76 | 85 |

A USP dissolution apparatus I (rotating baskets at 100 rpm) filled with deionized ("DI") water was used for the dissolution experiments. Experiments were carried out at 37° C. The analysis of the dissolution samples was performed using the UV method.

Example 3

Preparation of a Delayed Release/Extended Release Milnacipran Tablet Using Aqueous Granulation The ingredients, manufacturing process, and in vitro dissolution data for the extended release portion of a delayed release/extended release milnacipran pharmaceutical composition are described below (Lot Nos. 3 and 6, small scale manual batches; Lots Nos. 4 and 5, laboratory equipment scale):

| INGREDIENTS | Lot# 3 - bench | Lot# 4 - lab-equip | Lot# 5 - lab-equip | Lot# 6 - bench |
| --- | --- | --- | --- | --- |
| Milnacipran HCl | 120 mg | 120 mg | 120 mg | 120 mg |
| Hydroxypropyl Methylcellulose K100M | 80 mg | | 150 mg | 80 mg |
| Hydroxypropyl Methylcellulose E10M | 80 mg | 150 mg | | |
| Dibasic Calcium phosphate, Dihydrate | 150 mg | 118 mg | 98 mg | |
| Lactose, Anhydrous | | | | 98 mg |
| Ethocel ® 10 cps | | 52 mg | 52 mg | 52 mg |
| Povidone K 90 | 8 mg | 8 mg | | |
| Aquacoat ® 30D | | | 3.7 mg | 5.7 mg |
| Magnesium stearate | 6 mg | 6 mg | 6 mg | 6 mg |
| Total tablet weight | 444 mg | 454 mg | 429.7 mg | 431.7 mg |

The wet granulation process was performed as described in Example 1. The tablets were compressed using a single station bench top model tablet press.

Dissolution in Phosphate Buffer pH 6.8

| Dissolution time, hours | Milnacipran released, % of total dose | | | |
| --- | --- | --- | --- | --- |
| | Lot# 3 | Lot# 4 | Lot# 5 | Lot# 6 |
| 0.5 | 21 | 20 | 18 | 18 |
| 1 | 30 | 29 | 26 | 27 |
| 2 | 43 | 42 | 38 | 38 |
| 3 | 52 | 52 | 46 | 47 |
| 4 | 59 | 59 | 54 | 54 |
| 5 | 65 | 65 | 60 | 60 |
| 6 | 70 | 70 | 65 | 66 |
| 8 | 78 | 77 | 73 | 74 |
| 10 | 83 | 82 | 78 | 80 |
| 12 | 87 | 85 | 83 | 84 |
| 16 | 90 | 88 | 86 | 87 |
| 17 | 92 | 90 | 88 | 89 |

A USP dissolution apparatus I (rotating baskets at 100 rpm), filled with pH 6.8 phosphate buffer, was used for the dissolution experiments. Experiments were carried out at 37° C. The analysis of the dissolution samples was performed using the UV method.

Example 4

Preparation of an Alternative Delayed Release/Extended Release Milnacipran Tablet Using Aqueous Granulation The ingredients, manufacturing process, and in vitro dissolution data for the extended release portion of an alternative delayed release/extended release milnacipran pharmaceutical composition are described below (Lot #7, small scale manual batch; Lot # 8, pilot batch):

| Ingredients | Lot# 7 - manual batch mg per tablet | Lot# 8 - pilot scale mg per tablet |
| --- | --- | --- |
| Milnacipran HCl | 120 | 120 |
| Hydroxypropyl Methylcellulose K100M | 150 | 150 |
| Emcocel ® 50M | 98 | 98 |
| Ethocel ® 10 cps | 52 | 52 |
| Aquacoat ® 30D | 6 | 6 |
| Magnesium stearate | 6 | 6 |
| Total tablet weight | 432 | 432 |

The wet granulation process was performed as described in Example 1. The tablets were compressed using a single station bench top model tablet press. The pilot batch was prepared using a Zanchetta RotoP10 high shear granulator for the aqueous wet granulation process. The drying was performed in a Glatt GPCG-5 Fluid bed Granulator and the final blending was done using a "V" blender. The resulting blend was compressed using a rotary tablet press.

Dissolution in Phosphate Buffer pH 6.8

| | Milnacipran released, % of total dose | |
| --- | --- | --- |
| Incubation time, hours | Lot# 7 - manual batch | Lot# 8 - pilot scale |
| 0.5 | 16 | 16 |
| 1 | 23 | 25 |
| 1 | 35 | 37 |
| 3 | 44 | 46 |
| 4 | 52 | 55 |

-continued

| | Milnacipran released, % of total dose | |
|---|---|---|
| Incubation time, hours | Lot# 7 - manual batch | Lot# 8 - pilot scale |
| 5 | 58 | 62 |
| 6 | 64 | 67 |
| 8 | 72 | 77 |
| 10 | 78 | 84 |
| 12 | 83 | 89 |
| 14 | 87 | 92 |
| 16 | 89 | 95 |

A USP dissolution apparatus I (rotating baskets at 100 rpm), filled with pH 6.8 phosphate buffer, was used for the dissolution experiments. Experiments were carried out at 37° C. The analysis of the dissolution samples was performed using the UV method.

Example 5

Preparation of Alternative Delayed Release/Extended Release Milnacipran Using Aqueous Granulation The ingredients, manufacturing process, and in vitro dissolution data for an alternative delayed release/extended release milnacipran pharmaceutical composition are described below. The extended release cores were coated with Eudragit® L 100-55 (ACRYL-EZE®). Lot# 8 extended release core tablets (see Example 4) were coated in a 24" Accelacota Pan and samples with various delayed release coating contents (weight gain, w/w) were collected. The samples were subjected to in vitro dissolution tests that mimic the in vivo conditions to which the tablets are exposed when administered orally (approximately 2 hours in the stomach at acidic pH followed by approximately 16-18 hours in the intestines at neutral pH (Multiparticulate Oral Drug Delivery, 1994, Ghebre-Sellassie I., Ed., Marcel Dekker, Inc.; Wilding I. R., 2001, Adv. Drug Deliv. Rev., 46:103-124)).

A USP dissolution apparatus I (rotating baskets at 100 rpm) was used for the dissolution experiments. The dissolution media was 0.1 N HCl for the first 2 hours followed by pH 6.8 phosphate buffer. All dissolution tests were conducted at 37° C. The UV method was used for the analysis of the samples. Total drug released (%) is given as a function of the incubation time.

| Cumulative Incubation time, hours (beginning with 0.1 N HCl, changing to pH 6.8 buffer) | Lot# 9 6.36% (weight gain) DR coating | Lot# 10 8.39% (weight gain) DR coating | Lot# 11 10.29% (weight gain) DR coating | Lot# 12 11.01% (weight gain) DR coating | Lot# 13 12.74% (weight gain) DR coating |
|---|---|---|---|---|---|
| 0.1 N HCl | | | | | |
| 0.5 | 0 | 0 | 0 | 0 | 0 |
| 1 | 0 | 0 | 0 | 0 | 0 |
| 2 | 3 | 1 | 0 | 0 | 0 |
| pH 6.8 buffer | | | | | |
| 2.5 | 20 | 19 | 18 | 20 | 21 |
| 3 | 29 | 28 | 28 | 31 | 33 |
| 4 | 41 | 41 | 42 | 46 | 47 |
| 5 | 50 | 51 | 52 | 56 | 57 |
| 6 | 57 | 59 | 60 | 64 | 65 |
| 7 | 63 | 65 | 67 | 71 | 72 |
| 8 | 68 | 71 | 73 | 77 | 77 |
| 10 | 77 | 80 | 82 | 86 | 82 |
| 12 | 83 | 87 | 89 | 93 | 90 |
| 14 | 88 | 92 | 94 | 98 | 95 |
| 16 | 91 | 95 | 97 | 102 | 99 |
| 18 | 94 | 98 | 100 | 104 | 104 |

Example 6

An Alternative Extended Release Core Tablet

An alternative extended release core tablet was prepared as described above. Preferred values and ranges are described below.

Extended Release Core Tablet (Lot# 14-2,000 Tablets Pilot Batch)

| Ingredient | mg per core | % per core tablet | Preferred range, % per core tablet |
|---|---|---|---|
| Milnacipran HCl | 120 | 27.8 | 10-80 |
| HPMC K100 M premium | 150 | 34.7 | 5-45 |
| Avicel ® PH 102 | 98 | 22.7 | 5-55 |
| Ethocel ® 10 cps | 52 | 12.0 | 0-40 |
| Aqua coat ECD 30 | 6 | 1.4 | 0-10 |
| Magnesium stearate | 6 | 1.4 | 0.25-5 |
| Total extended release core tablet weight | 432 | | |

Example 7

An Alternative Delayed Release Coated Tablet

Lot# 14 extended release core tablets was used to prepare a pilot batch of enteric coated tablets. Delayed release/extended release tablets, Lot# 15 (2,000 tablets), were prepared as described above (see Example 5); however, an additional Opadry® seal coat was applied on the extended release core prior to delayed release coat application. Preferred values and ranges are provided below.

Delayed release coat for Lot# 15

| Ingredient | mg per core tablet | % weight gain per core tablet | Preferred range, % weight gain per core tablet |
|---|---|---|---|
| Opadry ® 7006 clear (Colorcon) | 8.6 | 2 | 0-10 |
| ACRYL-EZE ® | 34.6 | 8 | 4-20 |

Example 8

Alternative Extended Release Core Formulations

Alternative extended release core formulations containing 120 mg of Milnacipran HCl are listed in the table below (aqueous granulation).

| Lot No. | Avicel® PH 102 (Intragranular) | Starch1500 | HPMC K100M Premium | Avicel® PH 102 (Extragranular) | Mg Stearate | Purified Water | Other |
|---|---|---|---|---|---|---|---|
| | | | Inactive Ingredients mg/tablet | | | | |
| 16 | 23.58 | 23.58 | 70 | 156.84 | 6 | 0.017 | Batch size: 2000 tablets[1] |
| 17 | 23.58 | 23.58 | 60 | 166.84 | 6 | 0.017 | Batch size: 2000 tablets[1] |
| 18 | 23.58 | 23.58 | 35 | 191.84 | 6 | 0.017 | Batch size: 2000 tablets[1] |

[1]Tablets punched with 10-12 Kp hardness

Dissolution rates for the formulations above (Lot #s 16-18) are shown below:

Release of Uncoated Tablets

| Lot No. | % Released[1] pH 6.8 Buffer | | | | | | | | | |
|---|---|---|---|---|---|---|---|---|---|---|
| | 0.5 h | 1 h | 2 h | 3 h | 4 h | 5 h | 6 h | 7 h | 8 h | 12 h |
| 16 | 22 | 34 | 50 | 62 | 71 | 77 | 83 | 88 | 91 | 99 |
| 17 | 21 | 33 | 48 | 60 | 68 | 77 | 84 | 87 | 93 | 99 |
| 18 | 24 | 40 | 59 | 70 | 80 | 86 | 91 | 93 | 97 | — |

[1]As measured by High Performance Liquid Chromatography (HPLC)

Uncoated tablets (Lots #16 and 17) were first coated with Opadry® 7006 clear (2% weight gain) to give a seal coat and then coated with Acryl-EZE® 93018359 white (8%, 9% and 10% weight gain) to provide an enteric coat. Dissolution date for the tablets for Acryl-EZE® 93018359 white (8% weight gain) is shown below.

Release of Coated Tablets

| Cumulative Incubation time, hours (beginning with 0.1 N HCl, changing to pH 6.8 buffer) | Milnacipran released, % total[1] | |
|---|---|---|
| | Lot# 16-coated[2] | Lot# 17-coated[2] |
| 0.1 N HCl | | |
| 2 | 0 | 1 |
| 1 pH 6.8 buffer | | |
| 2.5 | 14 | 18 |
| 3 | 25 | 30 |
| 4 | 40 | 46 |
| 5 | 51 | 56 |
| 6 | 59 | 64 |
| 7 | 68 | 71 |
| 8 | 74 | 76 |
| 9 | 78 | 82 |
| 10 | 83 | 83 |
| 12 | 89 | 88 |
| 14 | 93 | 92 |
| 16 | 93 | |

[1]As measured by HPLC
[2]Coated with Opadry® 7006, 2% weight gain and Acryl-EZE® 93018359 white, 8% weight gain Example 9

Composition and In Vitro Dissolution Profile of the Preferred Formulation

The composition of the extended release ("ER") core of the final formulation is given in Table 2.

The tablet core was manufactured as follows:

1. Milnacipran hydrochloride and Ethocel® 10 cps were sifted through a #40 screen.
2. The sifted milnacipran and ethocel from step 1 were loaded into a Rapid mixer granulator and mixed for 2 minutes at slow speed.
3. The dry mix from step 2 was granulated with Aquacoat® ECD-30 and the required quantity of water and mixed at slow speed for 2 minutes. The wet mass was passed through a #12 screen.
4. The wet mass from step 3 was dried in a tray oven at 50° C. till the moisture content was between 1% and 1.5% by weight.
5. The dried granules from step 4 were passed through a #30 screen.
6. Methocel® K100M and Avicel® PH 102 were sifted through a #40 screen. The dried granules from step 5 and the sifted materials were loaded into a V-cone blender and mixed for 15 minutes without the intensifier bar.
7. Magnesium stearate was sifted through a #40 screen and added to the mixture from step 6. The mixture was mixed in a V-Cone blender for 2 minutes without the intensifier bar.
8. The final blend was compressed into tablets with an average tablet weight of 400 mg using a 10.5 mm round standard concave punch at a hardness of 10-12 Kp.

TABLE 2

Composition of ER core (Lot #18)

| No. | Ingredient | Quantity per tablet | Quantity per 2,000 tablets |
|---|---|---|---|
| 1 | Milnacipran HCl | 120 mg | 240 g |
| 2 | Ethocel® 10 cps | 52 mg | 104 g |
| 3 | Aquacoat® ECD 30 | 6 mg | 40 g |
| 4 | Purified water | q.s. | 3 ml |
| 5 | Methocel® K 100 M premium | 35 mg | 70 g |
| 6 | Avicel® PH 102 | 181 mg | 362 g |
| 7 | Magnesium stearate | 6 mg | 12 g |
| | ER core weight | 400 mg | |

Milnacipran ER cores were coated with Opadry® 7006 (seal coat) up to 2% weight gain and further coated with Acryl-Eze® 93018359 White (delayed release coat) up to 8% weight gain. The final weight of the DR-ER tablet was 441 mg.

The coating parameters are shown in the table below:

| Parameter | Seal coat | Over coat |
|---|---|---|
| Coating equipment | Ganscoater | Ganscoater |
| Quantity of tablets | 600 g | 612 g |
| Pan speed | 11-12 rpm | 11-12 rpm |
| Spray rate | 2 g/min | 1.5-2 g/min |
| Inlet temperature | 70° C. | 70° C. |
| Exhaust temp. | 41° C. | 40° C. |
| Spray off time | 1 second | 1 second |
| Spray on time | 300 seconds | 300 seconds |
| Pressure | 3 kg/cm$^2$ | 3 kg/cm$^2$ |
| Weight gain | 2% | 8% |

In vitro dissolution data for 120 mg Milnacipran HCl DR-ER Tablet

A USP dissolution Apparatus I (rotating baskets) at 100 rpm was used for the dissolution experiments. The dissolution media was 0.1 N HCl for the first 2 hours followed by pH 6.8 phosphate buffer. Values given below are the average of three independent dissolution experiments. All dissolution tests were conducted at 37° C. HPLC analysis was used to determine percent drug release. Milnacipran released from the tablet (% of total dose) is given as a function of the incubation time. The in vitro dissolution curve is given in FIG. 1.

Figure 1:
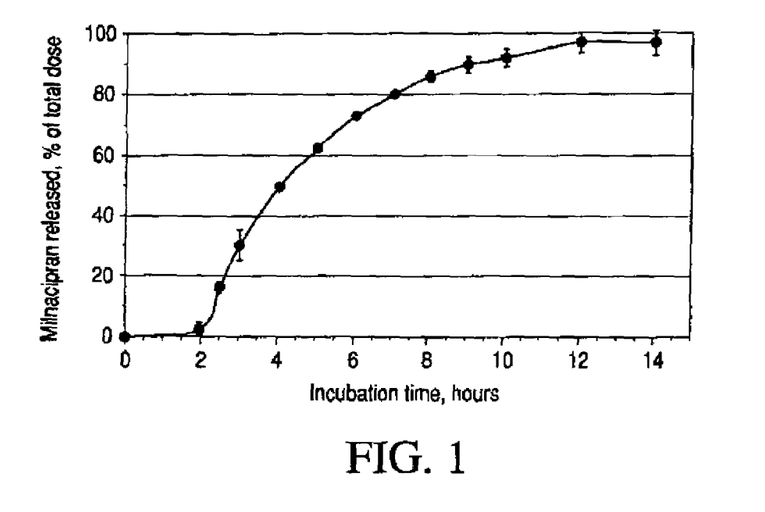
FIG. 1 is an in vitro dissolution profile of a 120 mg Milnacipran HCl DR-ER tablet. All dissolution tests were conducted at 37±0.5° C. HPLC analysis was used to determine drug release. Milnacipran released from the tablet (% of total dose) is given as a function of the incubation time.
Figure 2:
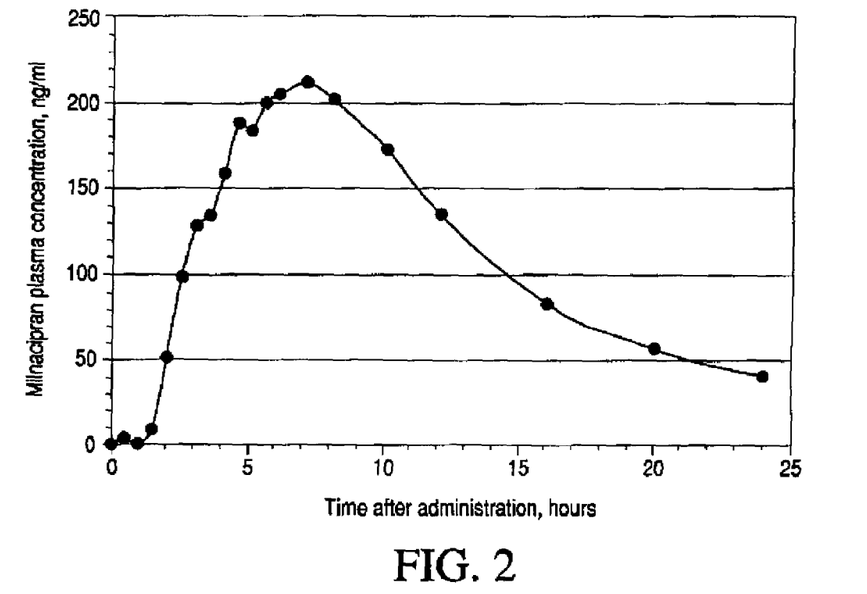
FIG. 2 is a graph of the mean milnacipran blood plasma concentration (ng/ml) over time (hours) following administration of a delayed release/extended release milnacipran formulation (120 mg milnacipran hydrochloride per tablet) to male healthy human subjects under fasting conditions.

| | Dissolution time, hours | | | | | | | | | | |
|---|---|---|---|---|---|---|---|---|---|---|---|
| | 2.0 | 2.5 | 3.0 | 4.0 | 5.0 | 6.0 | 7.0 | 8.0 | 9.0 | 10.0 | 12.0 | 14.0 |
| Milnacipran Released, % of Total Dose | 2 | 17 | 30 | 50 | 62 | 73 | 80 | 85 | 90 | 91 | 96 | 96 |

Example 10

Pharmacokinetic Parameters of Final Formulation in Healthy Human Volunteers

The Milnacipran DR-ER formulation (Lot #18) described above was tested in a single dose one way 6-patient pilot bioavailability study under fasting conditions. The calculated pharmacokinetic parameters were as follows: $T_{max}$ was 7±1 hours, $C_{max}$ was 220±40 ng/ml, AUC (0-24) was 2847 ng hr/ml, and AUC (0-inf) was 3084 ng hr/ml (Note that the data for five subjects were used to calculate the values above. The data for the 6$^{th}$ subject were not taken into account due to unexplainably low observed milnacipran plasma levels).

An IR milnacipran formulation was previously tested under fed conditions and it was found that administration of 50 mg Milnacipran HCl capsule BID resulted in an AUC (0-24) equal to 2592 ng hr/ml, and an AUC (0-inf) equal 2743 to ng hr/ml. Although no direct comparison can be made with the data obtained in the current study due to different study conditions (fasting vs. fed), the AUCs for DR-ER QD essentially matched the ones for IR BID. The known fact that food has very little influence on milnacipran absorption from IR dosage form further supports this statement.

It is important to note that none of the subjects at any given time during the bioavailability study (Lot #18) experienced any of common milnacipran side effects such as nausea, vomiting, sweating and tremors.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Although any methods and materials similar or equivalent to those described herein can be used in the practice or testing of the present invention, the preferred methods, devices, and materials are as described. Publications cited herein and the materials for which they are cited are specifically incorporated by reference.

We claim:

1. A milnacipran formulation comprising:
   (a) an extended release core comprising milnacipran, or a pharmaceutically acceptable salt thereof and one or more extended release excipients; and
   (b) a coating around the extended release core, said coating comprising a delayed release excipient;
   wherein:
   (i) the coating delays the rise in milnacipran blood plasma concentration for at least half-an-hour after administration to a patient in need thereof and causes the formulation to release in vitro less than 10% of the milnacipran over the first two hours measured in 0.1 N HCl;
   (ii) the extended release core allows a reduction in dosing frequency as compared to an immediate release dosage form; provides, upon administration to a human subject, a $T_{max}$ of about 6-10 hours; and produces therapeutically effective plasma levels over approximately 24 hours when administered to a patient in need thereof; and
   (iii) the formulation provides a diminished incidence or reduced intensity of one or more side effects effected by immediate release milnacipran.

2. The milnacipran formulation of claim 1, wherein the extended release excipient is an insoluble plastic, a hydrophilic polymer, a fatty compound, or mixtures thereof.

3. The milnacipran formulation of claim 2, wherein the insoluble plastic is methyl acrylate-methyl methacrylate co-polymer, polyvinyl chloride, polyethylene, or mixtures thereof.

4. The milnacipran formulation of claim 2, wherein the hydrophilic polymer is methyl cellulose, ethyl cellulose, hydroxypropyl cellulose, hydroxypropylmethylcellulose, sodium carboxymethylcellulose, cross-linked acrylic acid polymers, a polyethylene oxide, or mixtures thereof.

5. The milnacipran formulation of claim 1, wherein the delayed release excipient is a cellulosic polymer, an acrylic acid polymer, an acrylic acid copolymer, a methacrylic resin, a vinyl polymer, a vinyl copolymer, an enzymatically degradable polymer, zein, shellac, or mixtures thereof.

6. The milnacipran formulation of claim 5, wherein the delayed release excipient is a methacrylic resin.

7. The milnacipran formulation of claim 1, further comprising at least one diluent.

8. The milnacipran formulation of claim 1, wherein the side effects are nausea, vomiting, headache, tremulousness, anxiety, panic attacks, palpitations, urinary retention, orthostatic hypotension, diaphoresis, chest pain, rash, weight gain, back pain, constipation, vertigo, increased sweating, agitation, hot flushes, tremors, fatigue, somnolence, dyspepsia, dysoria, nervousness, dry mouth, abdominal pain, irritability, and insomnia.

9. The milnacipran formulation of claim 1, wherein the formulation provides a $C_{max}$ of approximately 220 ng/mL.

10. The milnacipran formulation of claim 1, further comprising at least one other active compound which is an analgesic, an anti-inflammatory, an antipyretic, an antidepressant, an antiepileptic, an antihistamine, an antimigraine drug, an antimuscarinic, an anxiolytic, a sedatives, a hypnotic, an antipsychotic, a bronchodilator, an anti asthma drug, a cardiovascular drug, a corticosteroid, a dopaminergic, an electrolyte, a gastro-intestinal drug, a muscle relaxant, a nutritional agent, a vitamin, a parasympathomimetic, a stimulant, an anorectic, or an anti-narcoleptic.

11. The milnacipran formulation of claim 1, wherein the formulation comprises 25 to 500 mg of milnacipran.

12. The formulation according to claim 1, wherein the milnacipran or a salt thereof is present in an amount effective to treat fibromyalgia.

13. The formulation according to claim 1, wherein the formulation provides, upon administration to a human subject, a $T_{max}$ of 7±1 hours.

14. The formulation according to claim 1, wherein the formulation provides, upon administration to a human subject, an area under the curve (AUC) (0-24) of less than 3000 ng hr/ml.

15. The formulation according to claim 1, wherein the formulation is in the form of a tablet.

16. The formulation according to claim 1, comprising a single unit dosage form.

17. The formulation of claim 1, wherein
the coating causes the formulation to have about a 6-12% weight gain.

* * * * *